United States Patent
Howes, Jr. et al.

(10) Patent No.: US 6,892,143 B2
(45) Date of Patent: May 10, 2005

(54) CONTROLLING CHEMICAL DISPENSE OPERATIONS BASED ON CONDUCTIVITY OFFSET

(75) Inventors: Ronald Bruce Howes, Jr., Minneapolis, MN (US); Robert Eugene May, Lakeville, MN (US); Jeff W. Peterson, Hudson, WI (US)

(73) Assignee: Ecolab Inc., Mendota Heights, MN (US)

( * ) Notice: Subject to any disclaimer, the term of this patent is extended or adjusted under 35 U.S.C. 154(b) by 152 days.

(21) Appl. No.: 10/444,823

(22) Filed: May 22, 2003

(65) Prior Publication Data

US 2004/0236522 A1 Nov. 25, 2004

(51) Int. Cl.$^7$ ............................................. G01N 31/00
(52) U.S. Cl. ............................. 702/31; 702/30; 702/22; 700/9; 700/80
(58) Field of Search ............................ 702/31, 25, 30, 702/22–23; 700/9, 80, 239, 265, 283; 340/853.3, 853.2, 870.07; 705/1

(56) References Cited

U.S. PATENT DOCUMENTS

| | | |
|---|---|---|
| 3,223,108 A | 12/1965 | Martz, Jr. |
| 3,645,669 A | 2/1972 | Rausch |
| 3,774,056 A | 11/1973 | Sample et al. |
| 4,194,242 A | 3/1980 | Robbins |
| 4,241,400 A | 12/1980 | Kiefer |
| 4,334,270 A | 6/1982 | Towers |
| 4,482,785 A | 11/1984 | Finnegan et al. |
| 4,509,543 A | 4/1985 | Livingston et al. |
| 4,597,046 A | 6/1986 | Musmanno et al. |
| 4,682,113 A | 7/1987 | Barben, II |
| 4,733,798 A | 3/1988 | Brady et al. |
| 4,739,478 A | 4/1988 | Roberts et al. |
| 4,756,321 A | 7/1988 | Livingston et al. |
| 5,014,211 A | 5/1991 | Turner et al. |
| 5,038,807 A | 8/1991 | Bailey et al. |
| 5,043,860 A | 8/1991 | Koether et al. |
| 5,077,525 A | 12/1991 | West et al. |
| 5,203,366 A | 4/1993 | Czeck et al. ................... 137/3 |
| 5,222,027 A | 6/1993 | Williams et al. ............ 700/239 |
| 5,345,379 A | 9/1994 | Brous et al. ................... 700/17 |

(Continued)

FOREIGN PATENT DOCUMENTS

GB          1508469          4/1978

OTHER PUBLICATIONS

"Services Provided by Jaytech, Inc.", at http://www.jaytech.com, 2 pages.
Clover Systems Inc.'s product description of InfAc, 4 pages, including specifications and features.
U.S. Appl. No. 09/692,550, filed Oct. 19, 2000, Howes, Jr. et al.
International Search Report dated Oct. 4, 2004.

*Primary Examiner*—John Barlow
*Assistant Examiner*—Hien Vo
(74) *Attorney, Agent, or Firm*—Merchant & Gould P.C.

(57) ABSTRACT

A system and method is disclosed for controlling chemical dispense operations based on a conductivity offset determined for a chemical solution. The chemical dispense operations are performed by or in conjunction with operation of a utility device, such as a warewashing machine. The chemical solution is formed in a solution tank device by combining water with at least one component chemical product. The conductivity offset, which is the conductivity of the water, is used to normalize the conductivity estimated for the chemical solution relative to the component chemical product in the solution. During various points in time during operation of the utility device, the normalized conductivity is compared to a conductivity setpoint, and if the normalized conductivity falls below the conductivity setpoint, a specified volume of the component chemical product is supplied to the solution tank.

60 Claims, 6 Drawing Sheets

U.S. PATENT DOCUMENTS

| | | |
|---|---|---|
| 5,370,267 A | 12/1994 | Schroeder |
| 5,370,743 A | 12/1994 | Usui et al. |
| 5,397,028 A | 3/1995 | Jesadanont |
| 5,404,893 A | 4/1995 | Brady et al. |
| 5,491,791 A | 2/1996 | Glowney et al. |
| 5,556,478 A | 9/1996 | Brady et al. |
| 5,625,659 A | 4/1997 | Sears |
| 5,625,908 A | 5/1997 | Shaw |
| 5,681,400 A | 10/1997 | Brady et al. ............ 134/18 |
| 5,694,323 A | 12/1997 | Koropitzer et al. ...... 705/400 |
| 5,695,091 A | 12/1997 | Winings et al. |
| 5,724,261 A | 3/1998 | Denny et al. |
| 5,745,381 A | 4/1998 | Tanaka et al. ........... 702/182 |
| 5,757,664 A | 5/1998 | Rogers et al. ........... 700/232 |
| 5,810,201 A | 9/1998 | Besse et al. |
| 5,826,749 A | 10/1998 | Howland et al. ......... 222/1 |
| 5,839,097 A | 11/1998 | Klausner ............ 340/825.69 |
| 5,875,430 A | 2/1999 | Koether |
| 5,939,974 A | 8/1999 | Heagle et al. |
| 5,945,910 A | 8/1999 | Gorra |
| 5,956,487 A | 9/1999 | Venkatraman et al. |
| 5,967,202 A | 10/1999 | Mullen et al. ........... 141/104 |
| 5,973,696 A | 10/1999 | Agranat et al. |
| 5,975,352 A | 11/1999 | Spriggs et al. ............ 222/23 |
| 5,980,090 A | 11/1999 | Royal et al. ............. 700/241 |
| 6,003,070 A | 12/1999 | Frantz |
| 6,061,668 A | 5/2000 | Sharrow .................. 705/400 |
| 6,133,555 A | 10/2000 | Brenn |
| 6,133,847 A | 10/2000 | Yang |
| 6,321,204 B1 | 11/2001 | Kazami et al. ............. 705/7 |
| 6,330,499 B1 | 12/2001 | Chou et al. |
| 6,356,205 B1 | 3/2002 | Salvo et al. |
| 6,357,292 B1 | 3/2002 | Schultz et al. |
| 6,377,868 B1 | 4/2002 | Gardner ................... 700/236 |
| 6,389,464 B1 | 5/2002 | Kirshnamurthy et al. |
| 6,498,567 B1 | 12/2002 | Grefenstette et al. |
| 6,618,754 B1 | 9/2003 | Gosling |
| 2001/0039501 A1 | 11/2001 | Crevel et al. |
| 2001/0047214 A1 | 11/2001 | Cocking et al. |
| 2001/0053939 A1 | 12/2001 | Crevel et al. |
| 2001/0054038 A1 | 12/2001 | Crevel et al.- |

CONTROLLING CHEMICAL DISPENSE OPERATIONS BASED ON CONDUCTIVITY OFFSET

TECHNICAL FIELD

The invention relates generally to a utility device, and more particularly to monitoring conductivity of a chemical solution associated with the utility device.

BACKGROUND

A warewashing machine is a utility dishwasher used in many restaurants, healthcare facilities and other locations to efficiently clean and sanitize cooking and eating articles, such as, dishes, pots, pans, utensils and other cooking equipment. Articles are placed on a rack and provided to a washing chamber of the warewashing machine. In the chamber, rinse agents and cleaning products are applied to the articles over a predefined period of time referred to as a "wash cycle." A wash cycle includes a cleaning cycle and a rinsing cycle. At least one cleaning product is applied to the articles during the cleaning cycle. The cleaning product is typically a chemical solution formed by dissolving one or more component chemical products in water. The term component chemical product is used broadly to encompass, without limitation, any type of detergent, soap or any other product used for cleaning and/or sanitizing.

At least one rinse agent is applied to the articles during the rinsing cycle. The rinse agent is typically water with one or more wetting and/or sanitizing agents. The article racks contain holes that enable the cleaning product and rinse agent to pass through the racks during the cleaning and rinsing cycles, respectively. At the end of the wash cycle, the rack is removed from the washing chamber so that other racks carrying other articles may be moved into the washing chamber. The wash cycle is then repeated for each of these subsequent racks. Wash cycles may be customized for specific types of racks and the articles that the racks carry.

The cleaning products (hereinafter, "chemical solutions") applied to the articles by the warewashing machine are formed and contained in a solution tank typically located on the underside of the warewashing machine. A wash module is provided above the solution tank and in the lower portion of the washing chamber. The wash module extracts a chemical solution from the tank and applies the solution to the articles contained in the rack during the cleaning cycle. Following the cleaning cycle, a rinse module, which is provided in the upper portion of the washing chamber, administers the rinsing cycle by applying a rinse agent to the articles thereby rinsing the chemical solution from the articles.

Percent concentration of each individual component chemical product within a chemical solution being used by a warewashing machine to clean and sanitize articles at a public facility is governed by various food and health regulations. The percent concentration of a particular component chemical product relative to a formed chemical solution is proportional to the mass of the component relative to the mass of water in the chemical solution. One generally accepted method for complying with these regulations involves controlling input of component chemical product(s) into the chemical solution based on conductivity measurements of the solution. Conductivity of a chemical solution is generally defined as the electrical behavior of the solution, and therefore, is defined herein as a combination of the inherent electrical behavior associated with the water and the electrical behavior associated with the component chemical product(s) forming the solution.

To meet the above-noted various food and health regulations, warewash controllers are employed to oversee operations performed during the wash cycles of conventional warewashing machines. Warewash controllers are often added to warewashing machines after the machines are deployed into a production environment in which the machines are intended for use. The warewash controllers are communicatively coupled to the rinse and wash modules such that control over operations of these modules is administered by the controller. The warewash controller is also communicatively coupled to a component dispenser and operable to control the component dispenser to dispense specified amounts of a component chemical product to the solution tank and/or wash chamber. The warewash controller senses information related to operation of the warewashing machine and uses this sensed information to operate the component dispenser in such a manner that the various food and health regulations are complied with.

A warewash controller may utilize either inductive probes or conductivity cells to sense information related to conductivity of a chemical solution within the solution tank. Typically, these probes or cells gather such information by sampling, preferably multiple times, a predetermined volume of the chemical solution to generate therefrom a voltage indicative of the conductivity of the chemical solution. The warewash controller then links this voltage to an associated conductivity reading for the chemical solution. The conductivity readings are averaged by the warewash controller to determine an average conductivity over a specified period in time. The warewash controller uses this average conductivity to estimate the percent concentration of the component chemical product relative to water in the solution. If the percent concentration of the component chemical product is below a range prescribed by governing regulations, the warewash controller controls dispensing of that component chemical product in order to force the percent concentration to the prescribed range.

The above-mentioned conventional process of controlling detergent dispensing based on an estimated percent concentration has been an effective mechanism for complying with regulations throughout the years. However, this process is problematic in that such control is based on somewhat inaccurate readings with respect to the estimated percent concentration of component chemical products in the chemical solution. As noted above, water is associated with an inherent conductivity, and this inherent conductivity is included in the conductivity readings derived from voltages generated in the inductive probes or conductivity cells. As such, the resulting estimated percent concentration of a component chemical product relative to water is often inaccurate insofar as this estimated percent concentration for the component chemical product is based on the electrical behavior of not only the component chemical product, but also the inherent conductivity of water into which the component chemical product is dissolved.

SUMMARY OF THE INVENTION

In accordance with the present invention, the above and other problems are solved by a system and method for controlling chemical dispense operations based on a conductivity offset determined for a chemical solution. The chemical solution is formed in a solution storage tank by combining water with at least one component chemical product. The conductivity offset is the inherent conductivity associated with the water. In an embodiment, the conductivity offset is calculated by sampling the water situated in the solution storage tank, but prior to the introduction of the component chemical product. The actual conductivity of the chemical solution is continuously determined at multiple timing instances during a predetermined time period by measuring conductivity of the chemical solution and then subtracting the conductivity offset from each of the conductivity measurements. The conductivity offset is therefore used to determine the actual conductivity of the chemical solution at each timing instance during the predetermined time period. During this time period, the determined actual conductivity for each timing instance is compared to a conductivity setpoint, and if the actual conductivity falls below the conductivity setpoint, a specified volume of the component chemical product is supplied to the solution storage tank.

In an embodiment, the present invention provides a method performed by a computer system for controlling conductivity of a chemical solution situated in a solution storage tank. The chemical solution is formed by combining at least one component chemical product with water in the solution storage tank. The method according to this embodiment includes determining the inherent conductivity associated with the water and, after the chemical solution is formed in the solution storage tank, measuring the conductivity of the chemical solution. The method then includes analyzing the inherent conductivity associated with the water, the measured conductivity of the chemical solution and a conductivity setpoint specified for the chemical solution to determine whether the component chemical product should be supplied to the solution storage tank.

In accordance with another embodiment, the present invention relates to a system for controlling conductivity of a chemical solution situated in a solution storage tank. The chemical solution is formed by dissolving at least one component chemical product in water in the solution storage tank. The system includes a sensor and a controller. The sensor senses information related to both the inherent conductivity of the water and the conductivity of the chemical solution. In an embodiment, the information related to the inherent conductivity of the water is sensed as the water is situated in the solution storage tank prior to the component chemical product being introduced therein. In this embodiment, the information related to the conductivity of the chemical solution is therefore sensed after the component chemical product has been input to the solution storage tank. The conductivity of the chemical solution indicates percent concentration of the component chemical product relative to water in the chemical solution.

The controller receives the information sensed by the sensor over communication lines communicatively coupling the sensor to the controller. The controller analyzes the sensed information related to the inherent conductivity of the water to render a conductivity reading for the water. Likewise, the controller analyzes the sensed information related to the conductivity of the chemical solution a conductivity reading for the chemical solution. The controller then analyzes the conductivity reading for the water, the conductivity reading for the chemical solution and a conductivity setpoint specified for the chemical solution to determine whether the component chemical product should be supplied to the solution storage tank. The conductivity setpoint indicates a desired percent concentration of the component chemical product relative to water in the chemical solution.

The invention may be implemented as a computer process, a computing system or as an article of manufacture such as a solid state, non-volatile memory device or a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process.

These and various other features as well as advantages, which characterize the present invention, will be apparent from a reading of the following detailed description and a review of the associated drawings.

DETAILED DESCRIPTION

The present invention and its various embodiments are described in detail below with reference to the figures. When referring to the figures, like structures and elements shown throughout are indicated with like reference numerals. Objects depicted in the figures that are covered by another object, as well as the reference annotations thereto, are shown using dashed lines.

In one embodiment, the present invention relates to measuring a conductivity offset for use in normalizing conductivity readings of a chemical solution being used or applied (to objects) by a utility device. In another embodiment, the present invention relates to controlling dispensing operations for a component chemical product based on the normalized conductivity reading. In either embodiment of the invention, the chemical solution is a cleaning product used by a utility device to clean and/or sanitize objects placed in or around the device. The chemical solution is defined herein as a combination of at least one component chemical product and water. In accordance with this embodiment, the utility device is described below as being a cleaning apparatus, and more particularly a commercial dishwasher, which is also referred to as a "warewashing machine." In this embodiment, logical operations of the present invention are performed by a warewash controller communicatively coupled to a component chemical product dispenser processor and/or a rinse module, wash module and/or various other processors used to effectuate operation of the warewashing machine. It should be appreciated, however, that the utility device may be any type of apparatus that prepares, formulates, allocates or otherwise utilizes a chemical solution to perform a task.

Figure 1:
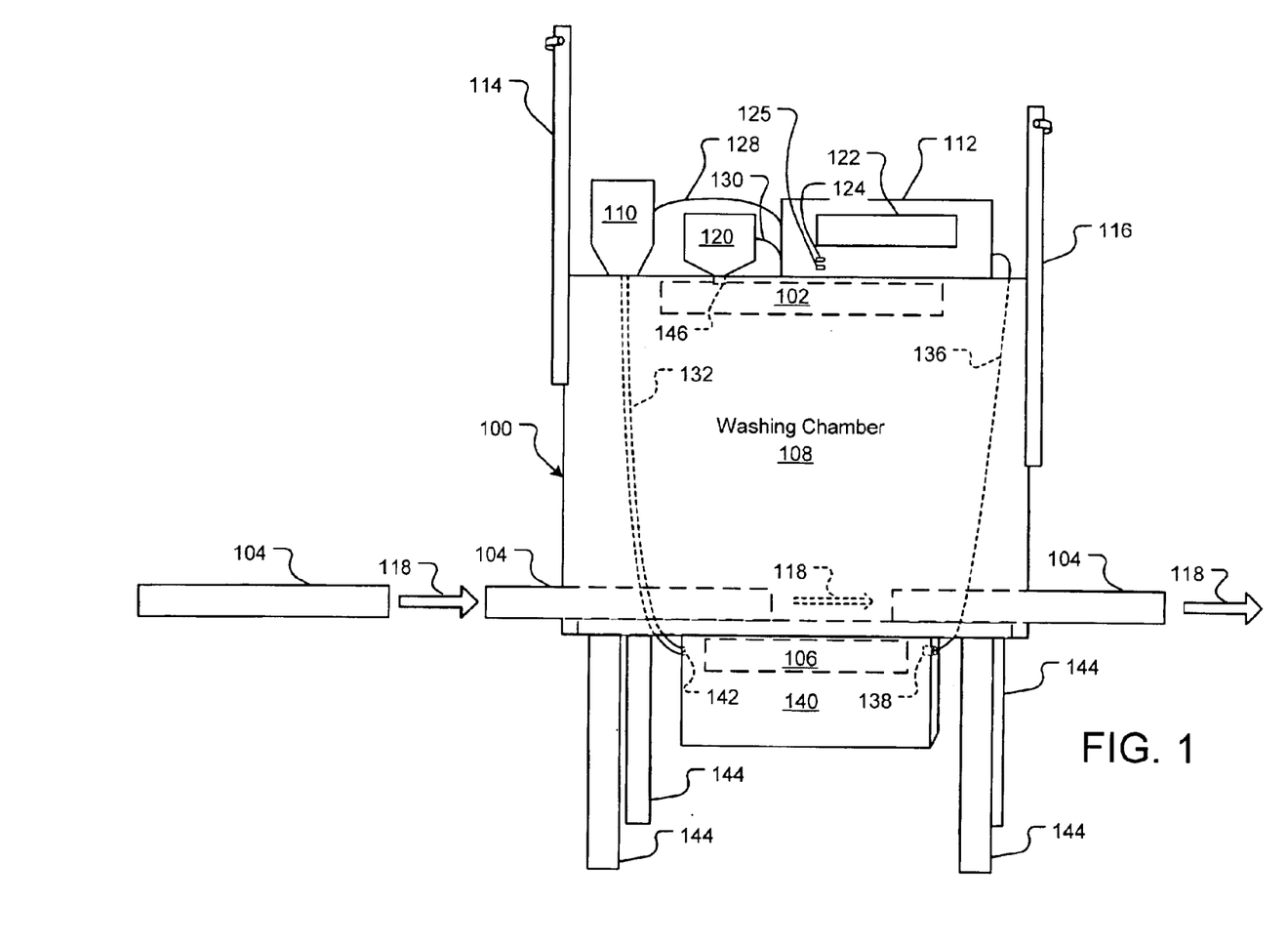
FIG. 1 illustrates components of a utility device in accordance with an embodiment of the present invention.

Referring now to FIG. 1, a warewashing machine 100 is shown in accordance with an embodiment of the present invention. The warewashing machine 100 is used to clean all types of dishware and kitchen objects, such as, without limitation, pots and pans used in restaurants, cafeterias and bakeries. Objects washed by the warewashing machine 100 are hereinafter referred to as "articles." The articles are provided to the warewashing machine 100 on article racks 104. The warewashing machine 100 may be any type of warewashing machine, such as, without limitation, a conveyor-type warewashing machine, a flight-type warewashing machine, a recirculating door-type warewashing machine, or a commercial dump or fill-type dish machine. For illustrative purposes, however, the warewashing machine 100 is described as being a conveyor-type warewashing machine with standard article racks 104. It should be appreciated that cleaning apparatus other than warewashing machines may be employed, including, for example, animal cage washers used in animal research areas.

The warewashing machine 100 includes a washing chamber 108, which, in the embodiment shown is enclosed by an entry sliding door 114 and an exit sliding door 116. The washing chamber 108 is supported above ground level by a plurality of legs 144. In operation, each article rack 104 carries one or more articles to be washed by the warewashing machine 100 into the washing chamber 108 through an opened entry sliding door 114. Arrows 118, which are provided in FIG. 1 for illustration purposes only, show the direction of article racks 104 through the washing chamber 108 in accordance with an embodiment of the present invention. Once an article rack 104 is located inside the washing chamber 108, the entry sliding door 114 and the exit sliding door 116 are both closed to fully contain the washing chamber 108 on all sides.

A rinse module 102 is provided within or directly above the washing chamber 108 for applying a rinse agent to articles placed in the article racks 104. Although water is hereinafter described as the exemplary rinse agent, it should be appreciated that the water may include wetting agent(s) and/or sanitizing agent(s) dissolved therein. A wash module 106 is provided within or directly below the washing chamber 108 for applying a chemical solution to articles placed in the racks 104. The chemical solution cleans the articles for subsequent use in eating, cooking or otherwise utilizing. In an embodiment, the rinse module 102 and the wash module 106 include arms (not shown) operably mounted to a spindle (not shown) for rotation about the spindle axis. The arms of the rinse module 102 include a plurality of openings (not shown) through which water is passed to articles placed in the washing chamber 108. Likewise, the arms of the wash module 106 include a plurality of openings (not shown) through which the chemical solution is passed to articles placed in the washing chamber 108.

The chemical solution is formed and stored in a solution tank 140 positioned underneath the washing chamber 108. The chemical solution is formed as a combination of water provided by the rinse module 102 and one or more component chemical products. For illustration purposes, and not by means of limitation, the chemical solution formed in the solution tank 140 is a combination of a single component chemical product and water. A drain (not shown) is positioned within the solution tank 140 to enable the flow of used chemical solution out of the solution tank 140 and into a chemical waste system, such as a septic tank or sewer. The act of removing the chemical solution from the solution tank 140 is referred to as "flushing." In accordance with various embodiments, the chemical solution may be automatically flushed after each wash process or after a predetermined number of wash processes, or alternatively, some warewashing machines may only allow manual flushing through the drain. The embodiment employed is a matter of implementation and it should therefore be appreciated that means for flushing solution out of the solution tank 140 is contemplated within the scope of the present invention.

Prior to being provided to the solution tank 140, the component chemical product used to form the chemical solution is stored in a product reservoir 110 in either a solid or liquid form. If the component chemical product is stored as a solid, water is applied to the product to liquefy the component chemical product such that the product may be provided to the solution tank 140 by way of a supply hose 132. Water is stored in a water reservoir 120 and dispensed into the washing chamber 108 by the rinse module 102. Water passes from the water reservoir 120 to the rinse module 102 by way of a coupling 146 therebetween. The rinse module 102 then applies the water to articles contained in a rack 104 situated in the washing chamber 108. An opening (not shown) is provided between the solution tank 140 and the washing chamber 108 to allow water provided to the washing chamber 108 to enter the solution tank 140. Water provided to the washing chamber 108 by the rinse module 102 passes through the opening into the solution tank 140, therein combining with pre-existing chemical solution to further dilute the chemical solution and therefore lower the concentration of component chemical product in the solution.

In an embodiment of the present invention, operations of the warewashing machine 100 are controlled by a warewash controller within a control box 112. In this embodiment, the control box 112 includes the warewash controller (internal to the control box 112) and one or more display devices or modules, such as, without limitation, first and second status indicators, e.g., light emitting diodes (LED's), 124 and 125 and a graphical user interface 122. The warewash controller performs operations stored as firmware or software to control and monitor various tasks administered by the warewashing machine 100 over a given wash cycle. For example, without limitation, in response to detecting initiation of a wash cycle for each rack 104 provided to the warewashing machine 100, the controller controls dispensing of the component chemical product to the solution tank 140. To accomplish this, the warewash controller measures conductivity of the chemical solution resident in the solution tank 140, and based on this measurement, controls the amount of the component chemical product dispensed to the solution tank 140. In an embodiment, the controller may also control initiation and operation of the wash module 106 and the rinse module 102 during each wash cycle performed by the warewashing machine 100. Furthermore, the warewash controller generates information for display on the graphical user interface 122 as well as first and second status indicators 124 and 125 based on the various tasks that the control box 112 controls and monitors. In an exemplary embodiment, the warewash controller is a special-purpose controller manufactured by NOVA Controls. However, it should be appreciated that the warewash controller may be any type or make of controller known to those skilled in the art.

In accordance with various embodiments, the warewash controller administers the aforementioned control and monitoring operations using a chemical product output control line 128, a water output control line 130 and a conductivity input control line 136, each input to the control box 112. The chemical product output control line 128 couples the control box 112 to a processor (not shown) responsible for dispensing the component chemical product from the product reservoir 110. Under direction of the warewash controller, the control box 112 transmits signals to the product reservoir processor over the chemical product output control line 128. These signals direct the product reservoir processor to dispense a particular volume of chemical product to the solution tank 140. If the component chemical product is stored in the product reservoir 110 in a solid form, the product reservoir processor activates a water pump that applies a predetermined volume of water to the solidified chemical product. Upon the application of this predetermined volume of water, an associated volume (with respect to the predetermined volume of water) of the component chemical product in a liquid form is created and dispensed out of the product reservoir 110.

The water output control line 130 couples the control box 112 to a processor (not shown) responsible for dispensing water from the water reservoir 120. In an embodiment, the water reservoir processor controls operation of a water pump (not shown) that pushes water through an output of the water reservoir 120 and into the rinse module 102. Under direction of the warewash controller, the control box 112 transmits signals to the water reservoir processor over the water output control line 130. These signals direct the water reservoir processor to activate the water pump to dispense a predetermined volume of water to the rinse module 102. Almost simultaneously and under the direction of the warewash controller, the control box 112 also directs the rinse module 102 to provide the water to the washing chamber 108 for application to articles contained in an article rack 104 currently situated therein. The water passes over the articles and to the solution tank 140, where the water combines with chemical solution already contained in the tank 140, thereby diluting the solution.

As the chemical solution resides in the solution tank 140, the warewash controller monitors concentration of the component chemical product relative to the chemical solution based on conductivity measurements. To accomplish this, the conductivity input control line 136 couples the control box 112 to an inductive probe 138 operable for sensing information, e.g., electrical properties, for use in determining the conductivity of the chemical solution. This sensed information, which is provided to the control box 112 over the conductivity input control line 136, is used by the warewash controller to calculate conductivity of the chemical solution. As such, information linking these electrical properties, e.g., generated voltages, to associated conductivity readings is stored within memory local to the warewash controller. Similarly, each conductivity reading is linked, directly or indirectly, to an associated percent concentration of the component chemical product. A target, or setpoint, conductivity reading (hereinafter "conductivity setpoint") is associated with the desired percent concentration for the component chemical product relative to water in the chemical solution. The warewash controller compares the conductivity setpoint to each conductivity measurement to determine whether, and if so, how much, component chemical product should be added to the solution to meet the conductivity setpoint, and thus, the desired percent concentration.

Inductive probes and the methods used by inductive probes to measure conductivity are well known in the art and not described in further detail herein. In an exemplary embodiment, the inductive probe 138 is a Model 28.740.7, manufactured by Lang Apparatebau GmbH. However, it should be appreciated that the inductive probe 138 may be any type or make of inductive probe known to those skilled in the art. Furthermore, the inductive probe 138 may be replaced in an alternative embodiment by one or more conductivity cells. For example, U.S. Pat. No. 4,733,798 teaches conventional electrode-bearing conductivity cells and electrode-less conductivity cells as well as use thereof in measuring conductivity of a chemical solution and controlling concentration of the component chemical product(s) contained therein.

In accordance with an embodiment, the control box 112 is also coupled to the rinse module 102 and the wash module 106 by way of communication links (not shown). Under direction of the warewash controller, the control box 112 controls operation of the rinse module 102 and the wash module 106 by issuing command signals to a processor (not shown) locally controlling the rinse module 102 and a processor (not shown) locally controlling the wash module 106. The command signals are transmitted to the processor over the aforementioned communication links. Based on such control, the warewash controller can determine when either the wash module 106 or the rinse module 102 are currently active, and therefore dispensing the chemical solution or water, respectively.

In an embodiment, the first and second status indicators 124 and 125 indicate the current operation of the warewashing machine 100. For example, the first status indicator 124 may indicate to users that the warewashing machine 100 is currently activated and in the middle of a wash cycle. The second status indicator 125 may indicate to users that the warewashing machine 100 is not only activated, but that the chemical product is currently being dispensed to the solution tank 140. It should be appreciated that the status indicators 124 and 125 may be used for any other purpose related to operating characteristics of the warewashing machine 100.

Like the status indicators 124 and 125, the graphical user interface 122 is used for presenting information to a user of the warewashing machine 100. However, with the graphical user interface 122, the amount of information that may be presented to a user is substantially greater than the information that may be presented by the status indicators 124 and 125. For instance, the graphical user interface 122 may present to a user a selection screen that enables the user to define or modify the conductivity setpoint value for the chemical solution.

The selection screen may also enable a user to define the amount of time for a wash cycle, the amount of time that the wash module 106 is active and the amount of time that the rinse module 102 is active. Various other parameters and operating conditions may be defined or selected by a user through the graphical user interface 122 including, without limitation, a temperature for the rinse agent, a rate at which conductivity is sensed, or monitored, by the inductive probe 138 operating in conjunction with the warewash controller, a rate in which a component chemical product is dispensed if the warewashing operations are time-based, e.g., in implementations where the control box 112 does not control dispensing based on information sensed by the inductive probe 138, a rate in which water is dispensed, and velocity of the revolution of wash and rinse arms about a spindle axis. In addition, the graphical user interface 122 may be used to limit operating access of the warewashing machine 100 to authorized users.

Operation of the warewashing machine 100 commences after both the entry sliding door 114 and the exit sliding door 116 are closed with a rack 104 being located substantially underneath the rinse module 102 and substantially above the wash module 106. Initially, the chemical solution is applied to the articles by the wash module 106. Application of the chemical solution to the articles is then maintained for a predetermined period in time. After the chemical solution 106 is applied to the articles, the rinse module 102 applies water to the articles in order to rinse the chemical solution away from the articles. Like the wash module 106, the rinse module 102 is operated for a predetermined period in time. In accordance with a first embodiment, the warewash controller is responsible for controlling and monitoring operations of the wash module 106 and the rinse module 102. That is, the warewash controller initiates both the wash module 106 and the rinse module 102 and controls the length in time that the chemical solution and rinse agent, respectively, are applied thereby. In accordance with a second embodiment, the warewash controller only monitors, and thus, does not control, these operations. Such monitoring is administered in this embodiment in order to perform the various other operations that the controller is responsible for, such as, without limitation, measuring conductivity and determining when and how much component chemical product to dispense to the tank 140. After the wash cycle is complete, the exit sliding door 116 is opened and the rack 104 may be removed from the washing chamber 108 to make the warewashing machine 100 available for use by subsequent article racks 104.

Figure 2:
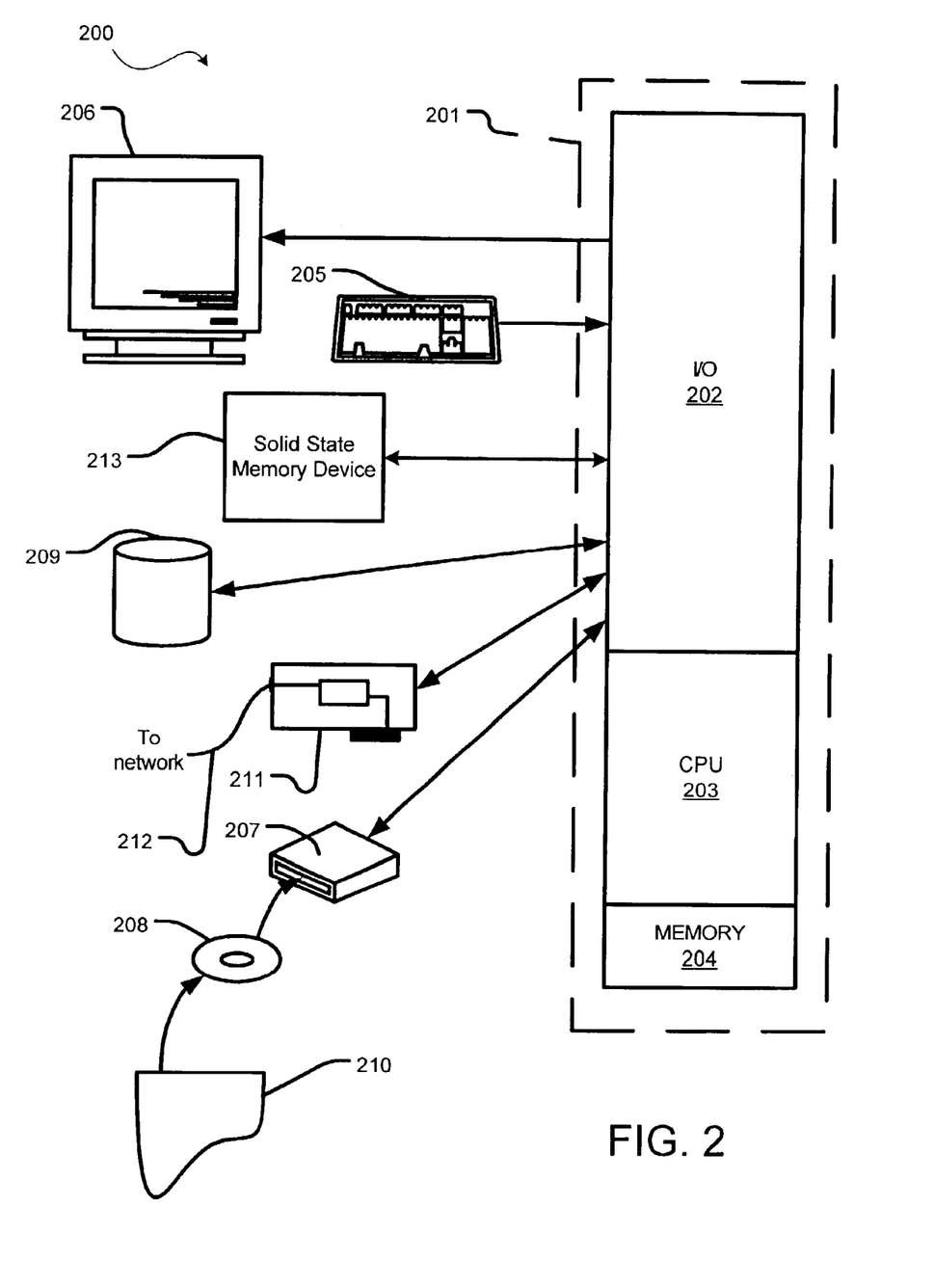
FIG. 2 depicts a general-purpose computer that implements logical operations of an embodiment of the present invention.

FIG. 2 depicts a computing system 200 capable of executing a program product embodiment of the present invention. One operating environment in which the present invention is potentially useful encompasses the computing system 200, such as, for example, the control box 112 or a remote computer to which information collected by the control box 112 may be uploaded. In such a system, data and program files may be input to the computing system 200, which reads the files and executes the programs therein. Some of the elements of a computing system 200 are shown in FIG. 2 wherein a controller (e.g., warewash controller), illustrated as a processor 201, is shown having an input/output (I/O) section 202, a microprocessor, or Central Processing Unit (CPU) 203, and a memory section 204. The present invention is optionally implemented in software or firmware modules loaded in memory 204 and/or stored on a solid state, non-volatile memory device 213, a configured CD-ROM 208 or a disk storage unit 209. As such, the computing system 200 is used as a "special-purpose" machine for implementing the present invention.

The I/O section 202 is connected to a user input module 205, e.g., a keyboard, a display unit 206 and one or more program storage devices, such as, without limitation, the solid state, non-volatile memory device 213, the disk storage unit 209, and the disk drive unit 207. The user input module 205 is shown as a keyboard, but may also be any other type of apparatus for inputting commands into the processor 201. The solid state, non-volatile memory device 213 is an embedded memory device for storing instructions and commands in a form readable by the CPU 203. In accordance with various embodiments, the solid state, non-volatile memory device 213 may be Read-Only Memory (ROM), an Erasable Programmable ROM (EPROM), Electrically-Erasable Programmable ROM (EEPROM), a Flash Memory or a Programmable ROM, or any other form of solid state, non-volatile memory. In accordance with one embodiment, the disk drive unit 207 is a CD-ROM driver unit capable of reading the CD-ROM medium 208, which typically contains programs 210 and data. Computer program products containing mechanisms to effectuate the systems and methods in accordance with the present invention may reside in the memory section 204, the solid state, non-volatile memory device 213, the disk storage unit 209 or the CD-ROM medium 208.

In accordance with an alternative embodiment, the disk drive unit 207 may be replaced or supplemented by a floppy drive unit, a tape drive unit, or other storage medium drive unit. A network adapter 211 is capable of connecting the computing system 200 to a network of remote computers via a network link 212. Examples of such systems include SPARC systems offered by Sun Microsystems, Inc., personal computers offered by IBM Corporation and by other manufacturers of IBM-compatible personal computers, and other systems running a UNIX-based or other operating system. A remote computer may be a desktop computer, a server, a router, a network PC (personal computer), a peer device or other common network node, and typically includes many or all of the elements described above relative to the computing system 200. Logical connections may include a local area network (LAN) or a wide area network (WAN). Such networking environments are commonplace in offices, enterprise-wide computer networks, intranets, and the Internet.

In accordance with a program product embodiment of the present invention, software instructions stored on the solid state, non-volatile memory device 213, the disk storage unit 209, or the CD-ROM 208 are executed by the CPU 203. In this embodiment, these instructions may be directed toward communicating data between a client and a server, detecting product usage data, analyzing data, and generating reports. Data, such as products usage data, corporate data, and supplemental data generated from product usage data or input from other sources, may be stored in memory section 204, or on the solid state, non-volatile memory device 213, the disk storage unit 209, the disk drive unit 207 or other storage medium units coupled to the system 200.

In accordance with one embodiment, the computing system 200 further comprises an operating system and usually one or more application programs. Such an embodiment is familiar to those of ordinary skill in the art. The operating system comprises a set of programs that control operations of the computing system 200 and allocation of resources. The set of programs, inclusive of certain utility programs, also provide a graphical user interface to the user. An application program is software that runs on top of the operating system software and uses computer resources made available through the operating system to perform application specific tasks desired by the user. In accordance with an embodiment, the operating system employs a graphical user interface 122 wherein the display output of an application program is presented in a rectangular area on the screen of the display device 206. The operating system is operable to multitask, i.e., execute computing tasks in multiple threads, and thus may be any of the following: Microsoft Corporation's "WINDOWS 95," "WINDOWS CE," "WINDOWS 98," "WINDOWS 2000" or "WINDOWS NT" operating systems, IBM's OS/2 WARP, Apple's MACINTOSH OSX operating system, Linux, UNIX, etc.

In accordance with the practices of persons skilled in the art of computer programming, the present invention is described below with reference to acts and symbolic representations of operations that are performed by the computing system 200, i.e., the control box 112 or a remote computer, unless indicated otherwise. Such acts and operations are sometimes referred to as being computer-executed. It will be appreciated that the acts and symbolically represented operations include the manipulations by the CPU 203 of electrical signals representing data bits causing a transformation or reduction of the electrical signal representation, and the maintenance of data bits at memory locations in the memory 204, the solid state, non-volatile memory device 213, the configured CD-ROM 208 or the storage unit 209 to thereby reconfigure or otherwise alter the operation of the computing system 200, as well as other processing signals. The memory locations where data bits are maintained are physical locations that have particular electrical, magnetic, or optical properties corresponding to the data bits.

The logical operations of the various embodiments of the present invention are implemented either manually and/or (1) as a sequence of computer-implemented steps running on a computing system, e.g., control box 112, and/or (2) as interconnected machine modules within the computing system. The implementation is a matter of choice dependent on the performance requirements of the computing system implementing the invention. Accordingly, the logical operations making up the embodiments of the present invention described herein are referred to alternatively as operations, acts, steps or modules. It will be recognized by one skilled in the art that these operations, structural devices, acts and modules may be implemented in software, in firmware, in special purpose digital logic, and any combination thereof without deviating from the spirit and scope of the present invention as recited within the claims attached hereto.

Figure 3:
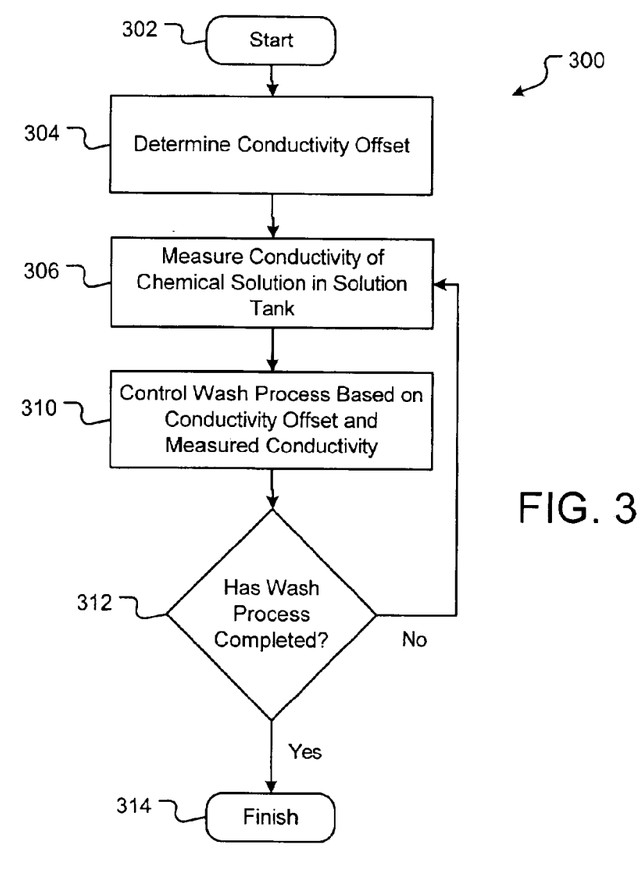
FIG. 3 is a flow diagram that illustrates operational characteristics for controlling application of a component chemical product for use in forming a chemical solution being used by a utility device in accordance with an embodiment of the present invention.

With the computing environment in mind, FIG. 3 illustrates operational characteristics of a process 300 for controlling application of a component chemical product for use in forming a chemical solution being used by a utility device in accordance with an embodiment of the present invention. The chemical solution is formed by dissolving the component chemical product in water in a storage tank ("solution storage tank").

For illustrative purposes, and not by means of limitation, the "control" process 300 is described below as a process for controlling operations associated with the warewashing machine 100 of FIG. 1. As such, the solution storage tank in which the chemical solution is formed and contained is the solution tank 140. In this embodiment, the logical operations of the control process 300 are performed by the warewash controller resident in the control box 112, which, as noted above, is communicatively coupled to one or more various processors (e.g., rinse module, wash module, product dispenser processor, etc.) of the warewashing machine 100. The component chemical product is provided to the solution tank 140 by a supply hose 132, through which the component product is supplied from a product reservoir 110 based on control instructions issued by the warewash controller to a product reservoir processor, as described above with reference to FIG. 1. In an embodiment, the water used to form the chemical solution is provided to the solution tank 140 by the rinse module 102 based on control instructions issued by the warewash controller to a processor locally directing water from a water reservoir 120 to the rinse module 102 by way of a coupling 146 therebetween. In another embodiment, operation of the rinse module 102 is controlled by the local processor and not by the warewash controller, which only passively monitors operation of the module 102.

The inherent conductivity of the water in which the component chemical product is dissolved in the solution tank 140 to form the chemical solution may vary based on geographic location of the origin of the water. The hardness-softness of the water, as well as the particles, e.g., ions, minerals, etc., contained within the water play a role in defining the inherent conductivity of the water. Typically, these parameters vary not only over disperse geographic locations, but also based on the source, e.g., well, treatment plant, river/creek bed, etc., of the water. The present invention, as described by the control process 300, provides an accurate means for determining the actual conductivity of the chemical solution relative to the component chemical product regardless of the source and geographic origin of the component water.

It should be appreciated that the control process 300 may be administered to control operations of any type of utility device wherein a chemical solution is formed and/or stored in a solution storage tank for use or application by the device to administer some task. In these other embodiments, the logical operations of the control process 300 are performed by a controller, such as the processor 201, responsible for controlling operations of these other types of utility devices. Some exemplary utility devices, in addition to a warewashing machine, which may be controlled by the control process 300 include, without limitation, a laundry machine, a chemical dispense system, a clean in place system, etc.

The control process 300 is performed with an operation flow beginning with a start operation 302 and concluding with a terminate operation 314. The start operation 302 is initiated when the warewashing machine 100 is initially deployed in a production environment where the machine 100 is intended for use therein. More specifically, the control process 300 begins as the warewash controller is first activated to control operations of the warewashing machine 100. In an embodiment, the warewash controller is activated by a field service technician through commands input through the graphical user interface 122. From the start operation 302, the operation flow passes to a determine offset operation 304.

The determine offset operation 304 calculates a conductivity reading associated with the water that is to be mixed with the component chemical product to form the chemical solution. This conductivity reading is hereinafter referred to as a "conductivity offset." FIG. 4, below, illustrates a process 400 for determining this conductivity offset in more detail in accordance with an embodiment of the present invention. After the conductivity offset is determined, the warewashing machine 100 is placed into operation in the production environment. At this time, the operation flow passes to a sense conductivity operation 306.

The sense conductivity operation 306 is initiated at the beginning of a first wash process following determination of the conductivity offset. As such, the solution tank 140 of the warewashing machine 100 is filled with both water and component chemical product concurrently with the initiation of the sense conductivity operation 306. After the level of chemical solution within the solution tank has risen above the conductivity probe 138, the sense conductivity operation 306 gathers samples of the chemical solution over a predetermined period in time, and using these samples, measures the conductivity of the chemical solution in multiple instances (for each sample) during the predetermined period in time. These conductivity measurements are averaged to render an average conductivity reading over the predetermined period in time. As noted above, these conductivity measurements, or the average thereof, are indicative of the percent concentration of the component chemical product relative to water in the chemical solution. As such, there exists in memory of the warewash controller a data structure, e.g., table, formula, etc., for matching all possible conductivity readings for the chemical solution to an appropriate percent concentration of the component chemical product relative to the component water. After the average conductivity reading for the predetermined period in time is determined, the operation flow passes to a control operation 310.

The control operation 310 renders control decisions associated with the wash process based on an analysis of the average conductivity reading for the chemical solution against a conductivity setpoint, taking into consideration the determined conductivity offset. To accomplish this, the control operation either "normalizes" the conductivity setpoint or the average conductivity reading based on the conductivity offset, as described in greater detail with respect to FIG. 5. The conductivity setpoint defines a target, or "desired," percent concentration for the component chemical product relative to water in the chemical solution.

For sake of illustration, the control operation 310 is hereinafter described with the average conductivity reading for the chemical solution being "normalized" by the conductivity offset to render an actual conductivity reading for the chemical solution. The actual conductivity reading for the chemical solution more accurately reflects the conductivity of the solution relative to the component chemical product, and therefore, more accurately may be used to determine the actual percent concentration of the component chemical product in the chemical solution. To determine the actual conductivity reading for the chemical solution relative to the component chemical product, the control operation 310 subtracts the conductivity offset from the average conductivity reading. As such, the average conductivity reading for the chemical solution is "normalized" based on the conductivity of the component water.

In this illustrative embodiment, the control operation 310 compares the actual conductivity reading for the chemical solution against the conductivity setpoint. In an embodiment, the conductivity setpoint is loaded into memory of the warewash controller prior to deployment in the production environment and based on several factors, including, without limitation, the chemical solution, the hardness/softness of the component water, the soil level of articles onto which the chemical solution is intended for application, etc. In other embodiments, the conductivity setpoint may be dynamically loaded into the warewash controller by users through the graphical user interface 122 and may be based on any number of other factors. Indeed, the conductivity setpoint may be based on user preference.

If, based on the comparison by the control operation 310, the actual conductivity reading for the chemical solution is less than the conductivity setpoint, then the control operation 310 commands the product reservoir dispenser processor to dispense a specified quantity of component chemical product to the solution tank 140. This specified quantity is derived based on the relative discrepancy between the actual conductivity reading and the conductivity setpoint.

From the control operation 310, the operation flow passes to a query operation 312. The query operation 312 determines whether the wash process has completed. If the wash process has completed, the operation flow concludes at the terminate operation 314. Otherwise, the operation flow passes back to the sense conductivity operation 306 and continues as previously described.

In an embodiment, the sense conductivity operation 306 and the control operation 310 are performed multiple times during a single wash process such that the conductivity of the chemical solution is repetitively tested against and directed toward the conductivity setpoint. For exemplary purposes, the control process 300 is shown as being performed during a single wash process of the warewashing machine 100. Although it is definitely contemplated by the present invention to perform all operations of the control process 300 for each particular wash process, a preferred embodiment includes performing the determine offset operation 304 for only a limited number of wash processes spread out over time periods in which the warewashing machine 100 is in use. As such, in this embodiment, the operation flow starts, except for the specific time points when an offset is determined, at the sense conductivity operation 306. Thus, a particular determined offset would be used to normalize the conductivity of the chemical solution measured during multiple wash processes. Such an embodiment is illustrated in more detail in FIG. 5.

Figure 4:
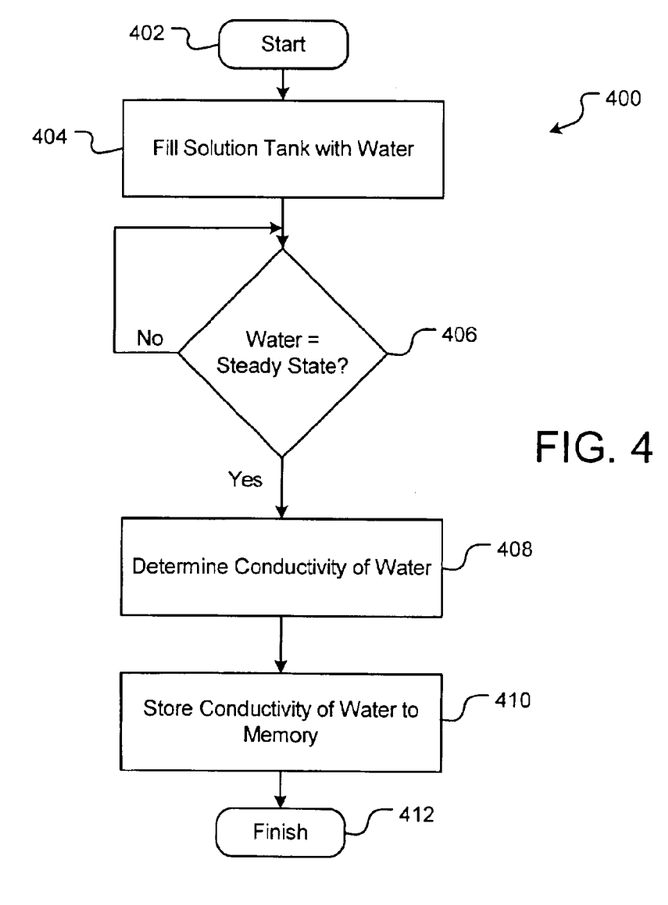
FIG. 4 is a flow diagram that illustrates operational characteristics for determining conductivity offset use in the process of FIG. 3 in accordance with an embodiment of the present invention.

Turning now to FIG. 4, a process 400 for determining conductivity offset is shown in accordance with an embodiment of the present invention. Specifically, the "offset determination" process 400 describes in more detail operations performed during the determine offset operation 304 of the control process 300 shown in FIG. 3. As with the control process 300, the logical operations of the offset determination process 400 are performed by the warewash controller in accordance with an embodiment of the present invention. The offset determination process 400 is performed with an operation flow beginning with a start operation 402 and ending with a terminate operation 412. The start operation 402 is initiated as the operation flow for the control process 300 passes to the determine offset operation 304. From the start operation 402, the operation flow immediately passes to a fill tank operation 404.

In an embodiment wherein the warewash controller controls operation of the rinse module 102, the fill tank operation 404 controls the application of water to the solution tank 140 such that the inductive probe 138 is covered by the water. In an embodiment wherein the warewash controller only monitors operation of the rinse module 102, the fill tank operation 404 monitors the application of water to the solution tank 140 to determine when the inductive probe 138 is covered by water. After the level of water in the solution tank 140 rises above the inductive probe 138, the operation flow passes to a query operation 406. The query operation 406 serves as a time delay in the process 400 wherein the process 400 is halted until the water in the solution tank 140 reaches steady state. Steady state is reached when the particles, e.g., ions, minerals, etc., within the water are uniformly dispersed throughout the water in the tank 140. As the water in the tank 140 reaches steady state, the operation flow passes to a determine conductivity operation 408.

The determine conductivity operation 408 uses the inductive probe 138 to sense conductivity-related information, e.g., voltage, in one or more samples of the water at steady state in the solution tank 140. The determine conductivity operation 408 then uses this conductivity-related information to calculate a conductivity measurement for each sample. Next, the determine conductivity operation 408 averages these conductivity measurements to render an average conductivity reading for the water. This average conductivity reading for the water is referred to as the "conductivity offset." After the conductivity offset is determined, the operation flow passes to a data store operation 410.

Figure 5:
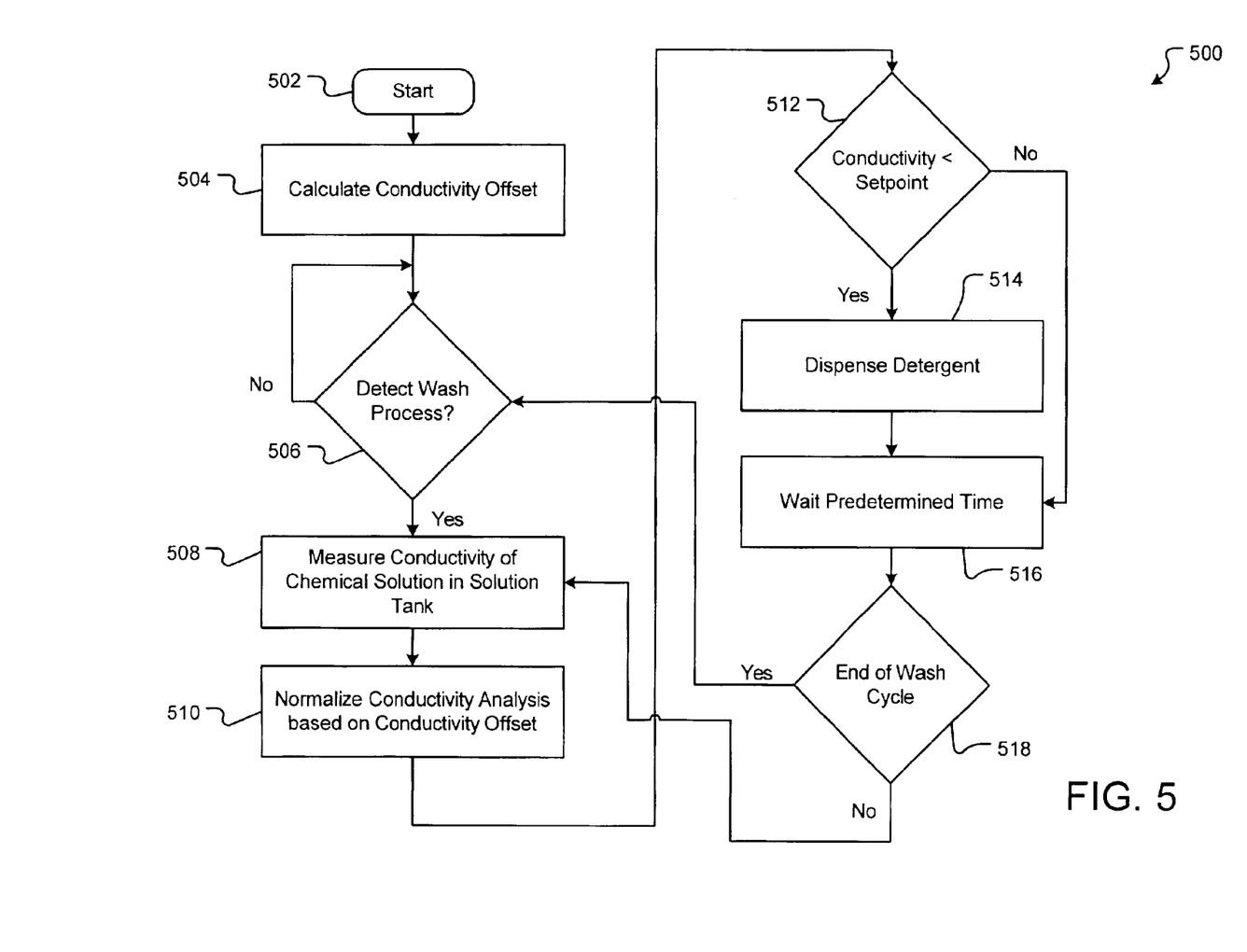
FIG. 5 is a flow diagram that illustrates operational characteristics shown in FIG. 3 in more detail in accordance with an embodiment of the present invention.
Figure 6:
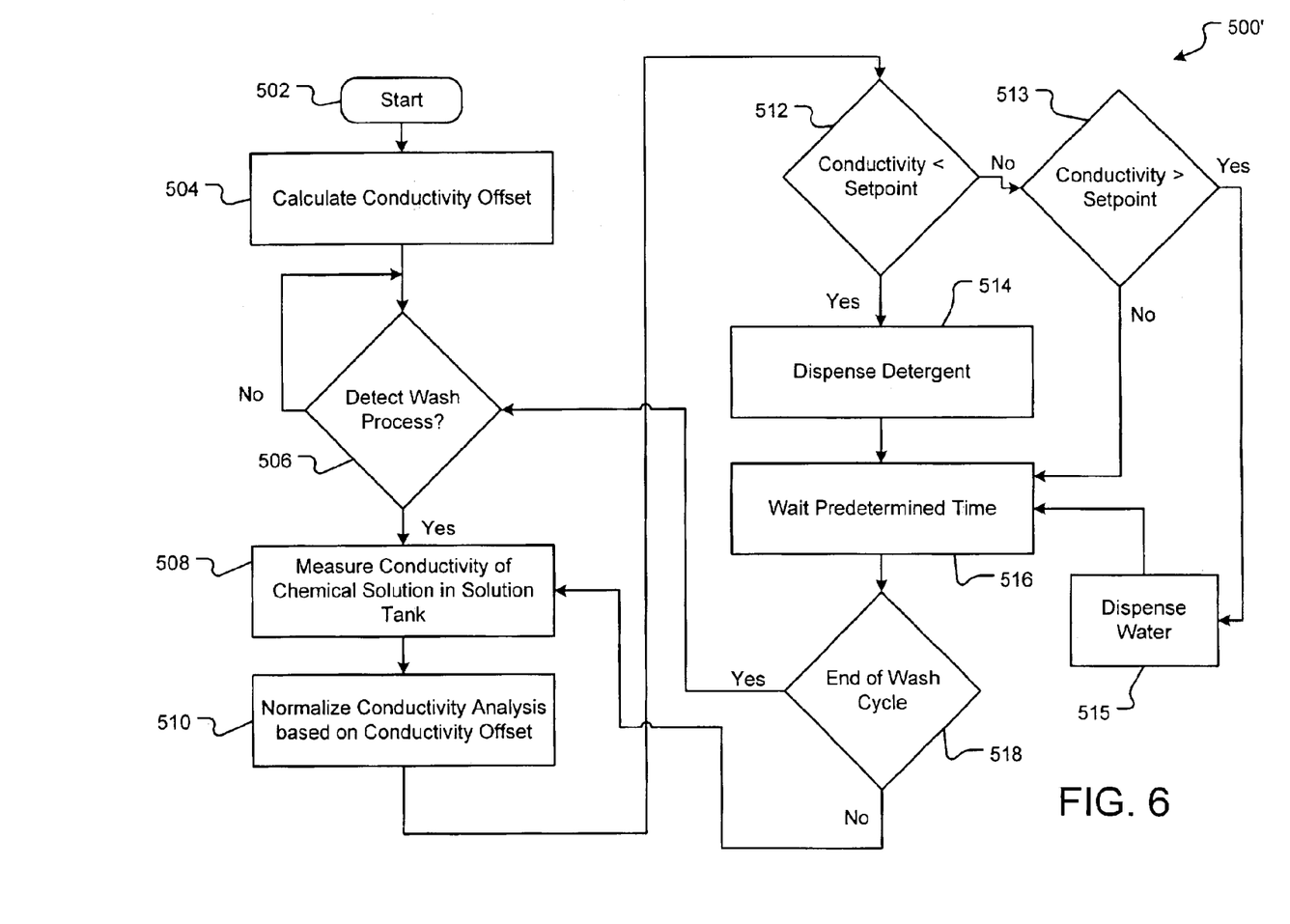
FIG. 6 is a flow diagram that illustrates operational characteristics shown in FIG. 5 in accordance with an alternative embodiment of the present invention.

The data store operation 410 saves the conductivity offset to memory within the warewash controller for subsequent use in controlling when the component chemical product is dispensed to the solution tank 140, as described in FIGS. 3, 5 and 6. From the data store operation 410, the operation flow of the offset determination process 400 concludes at the terminate operation 412, where the warewashing machine is placed into operation in the production environment and the operation flow of the control process 300 passes to the sense conductivity operation 306.

Referring now to FIG. 5, a process 500 for controlling application of a component chemical product for use in forming a chemical solution being used by a utility device is shown in accordance with an embodiment of the present invention. The "control" process 500 illustrates the control process 300 shown in FIG. 3 in more detail in accordance with an embodiment of the present invention. In this embodiment, the control process 500 illustrates the repetitive nature of controlling application of the component chemical product using a conductivity offset reading measured once prior to initial operation of the utility device in the production environment. As such, the control process 500 does not conclude at a termination operation, as shown in the control process 300 of FIG. 3. The control process 500 is performed with an operation flow that begins with a start operation 502. As with the control process 300, the control process 500 is illustrated with the utility device being the warewashing machine 100.

The start operation 502 is initiated when the warewashing machine 100 is initially deployed in a production environment where the machine 100 is intended for use therein. Thus, the control process 500 begins as the warewash controller is first activated to control operations of the warewashing system. From the start operation 502, the operation flow passes to a calculate offset operation 504.

The calculate offset operation 504 calculates a "conductivity offset" associated with the water that is to be used to form the chemical solution. FIG. 4, above, illustrates an exemplary process 400 for determining conductivity offset in accordance with an embodiment of the present invention. After the conductivity offset is determined, the warewashing machine 100 is placed into operation in the production environment. At this time, the operation flow passes to a first query operation 506.

The first query operation 506 serves as a time delay in the control process 500 wherein the process is halted until the warewash controller initiates a wash process in the warewashing machine 100. In an embodiment, a wash process is initiated each time an article rack is provided to the washing chamber 108 for cleaning. Upon detection that a wash process is initiated, the operation flow passes to a sense conductivity operation 508. The sense conductivity operation 508, which in an embodiment, is implemented in part by the inductive probe 138, gathers samples of the chemical solution from the solution tank 140 over a predetermined period in time. Using these samples, the sense conductivity operation 508 measures the conductivity of the chemical solution during the predetermined period in time.

In an embodiment, the conductivity measurement calculated by the sense conductivity operation 508 is an average conductivity reading derived from the conductivity measurements of each of the gathered samples. After the average conductivity reading for the chemical solution over the predetermined period in time is estimated, the operation flow passes to a normalize operation 510.

In a first embodiment, the normalize operation 510 determines an actual conductivity reading for the chemical solution by subtracting the conductivity offset from the average conductivity reading for the chemical solution. As such, the average conductivity reading for the chemical solution is "normalized" based on the conductivity of the component water.

In a second embodiment, the normalize operation 510 normalizes the conductivity setpoint for the chemical solution rather than the average conductivity reading. As generally defined above, the conductivity setpoint is defined by the target, or "desired," percent concentration of the component chemical product relative to water in the chemical solution. In this embodiment, the normalize operation 510 adds the conductivity offset to the conductivity setpoint. The conductivity setpoint may be based on any number of factors, but, in an embodiment of the invention, relates to the degree of soil expected on the articles that are to be washed by the warewashing machine, the chemical solution that is to be applied thereto, and the physical qualities of the water (e.g., hardness, softness, etc.) being used to form the chemical solution.

Regardless of the embodiment, the operation flow passes from the normalize operation 510 to a second query operation 512. The second query operation 512 analyzes the relationship of the conductivity of the chemical solution to the conductivity setpoint. If the normalize operation 510 normalized the average conductivity reading for the chemical solution to the conductivity offset, then the second query operation 512 determines whether the "normalized" conductivity measurement is less than the conductivity setpoint. Likewise, if the normalize operation 510 normalized the conductivity setpoint to the conductivity offset, then the second query operation 512 determines whether the conductivity reading for the chemical solution is less than the "normalized" conductivity setpoint. In either case, if the conductivity of the chemical solution is less than the conductivity setpoint, the operation flow passes to a dispense product operation 514. Otherwise, the operation flow passes to a pause operation 516.

The dispense product operation 514 commands the processor for the product dispense reservoir 110 to dispense a specified quantity of component chemical product to the solution tank 140. The specified quantity is based on the relative discrepancy between the conductivity of the chemical solution and the conductivity setpoint, taking into account the conductivity offset. From the dispense product operation 514, the operation flow passes to the pause operation 516.

The pause operation 516 pauses the control process 500 for a predetermined period in time. This predetermined period in time may be either zero to infinite units (e.g., seconds, minutes, days, etc.). After the predetermined period in time, the operation flow passes to a fourth query operation 518.

The fourth query operation 518 determines whether the wash process detected in the first query operation 506 is still being performed. If the wash process has finished performing, the operation flow passes back to the first query operation 506 and continues as previously described once a new wash process is detected. Otherwise, if the wash process has not yet finished, the operation flow passes back to the sense conductivity operation 510 and continues as previously described to further test against and direct the conductivity of the chemical solution toward the established conductivity setpoint.

It will be clear that the present invention is well adapted to attain the ends and advantages mentioned, as well as those inherent therein. While a presently preferred embodiment has been described for purposes of this disclosure, various changes and modifications may be made which are well within the scope of the present invention. For example, the control process 500 shown in FIG. 5 may be modified to include operations for more accurately controlling the conductivity of a chemical solution resident in a storage tank, as shown in FIG. 6 in accordance with an embodiment of the present invention. In this embodiment, the modified control process 500' includes a third query operation 513 and a dispense water operation 515, both of which are described in further detail in the next paragraph. Such an embodiment is particularly useful when the utility device using or applying the chemical solution is a clean-in-place system or a chemical dispense system. It should be appreciated, however, that the modified control process 500' may also be implemented with any type of utility device which uses or applies a chemical solution to articles or objects. For instance, the modified control process 500' may be used with warewashing machines, laundry machines, etc.

In the embodiment shown in FIG. 6, the modified control process 500' includes all operations of the control process 500 shown in FIG. 5. In this modified control process 500', the operation flow is modified such that the "no" branch from the second query operation 512 passes the operation flow to the third query operation 513 rather than the pause operation 516.

The third query operation 513 analyzes the relationship of the conductivity of the chemical solution to the conductivity setpoint to determine whether the conductivity of the chemical solution is greater than the conductivity setpoint, taking into account the conductivity offset. If the normalize operation 510 normalized the average conductivity reading for the chemical solution to the conductivity offset, then the third query operation 513 determines whether the "normalized" conductivity measurement is greater than the conductivity setpoint. Likewise, if the normalize operation 510 normalized the conductivity setpoint to the conductivity offset, then the third query operation 513 determines whether the conductivity reading for the chemical solution is greater than the "normalized" conductivity setpoint. In either case, if the conductivity of the chemical solution is greater than the conductivity setpoint, the modified operation flow passes to the dispense water operation 515. Otherwise, the modified operation flow passes to the pause operation 516 and continues as described with reference to FIG. 5

The dispense water operation 515 commands the rinse module to dispense a specified quantity of water to the washing chamber 108. The specified quantity is based on the relative discrepancy between the conductivity of the chemical solution and the target percent concentration, taking into account the conductivity offset. From the dispense water operation 515 the modified operation flow passes to the pause operation 516 and continues as described with reference to FIG. 5.

Additionally, the warewash controller of the control box 112 is described herein as a processor 201, but may be replaced by or include conventional electrical and electronic devices/components, such as, without limitation, programmable logic controllers (PLC's) and logic components. In these embodiments, the logical operations of the present invention described in FIGS. 3, 4, 5 and 6 are administered by these conventional electrical and electronic devices/components.

In accordance with one embodiment, an operation for automatically resetting the conductivity offset may be employed within the control process 500. In this embodiment, the operation flow may pass from the fourth query operation 518 to the calculate offset operation 504 upon detection that a wash process has ended if the sensed conductivity in the solution tank reaches zero and the temperature detected in the solution tank equals room temperature. In such a circumstance, the solution tank is presumed empty, and therefore this would be an optimal time to recalibrate the conductivity offset.

In accordance with yet another embodiment, the controller (such as warewash controller) connects to a communications network by way of a network interface, such as the network adapter 211 shown in FIG. 2. Through this network connection, the controller is operable to transmit information to one or more remote computers, such as, without limitation, a server computer or user terminals. Various types of information may be transmitted from the controller to these remote computers over the network connection including, without limitation, data related to the analysis of the conductivity measurements against the conductivity setpoint in both embodiments where either parameter is normalized by the conductivity offset, the average conductivity measurements, the conductivity setpoint for various component chemical products used by the utility device controlled by the controller, the measured conductivity offsets for water, etc. In addition, the network adaptor 211 enables users at remote computers the ability to issue commands to the controller. For example, a user at a remoter computer may modify the conductivity setpoint using this network connection.

Numerous other changes may be made which will readily suggest themselves to those skilled in the art and which are encompassed in the spirit of the invention disclosed and as defined in the appended claims.

What is claimed is:

1. In a computer system, a method for controlling conductivity of a chemical solution situated in a solution storage tank, the chemical solution being formed by combining at least one component chemical product with water in the solution storage tank, the method comprising:

determining a conductivity measurement associated with the water;

after the chemical solution is formed in the solution storage tank, calculating a conductivity measurement for the chemical solution, wherein the conductivity measurement indicates a percent concentration of the component chemical product relative to water in the chemical solution; and analyzing the conductivity measurement associated with the water, the conductivity measurement of the chemical solution and a conductivity setpoint specified for the chemical solution to determine whether the component chemical product should be supplied to the solution storage tank, wherein the conductivity setpoint indicates a desired percent concentration of the component chemical product relative to water in the chemical solution.

2. A method as defined in claim 1, wherein the act of determining a conductivity measurement associated with the water comprises:

prior to supplying the component chemical product to the solution storage tank, filling the solution storage tank with the water and analyzing one or more samples of the water to generate information related to the conductivity of the water.

3. A method as defined in claim 2, wherein the act of determining a conductivity measurement associated with the water further comprises:

analyzing the information related to the conductivity of the water to render the conductivity measurement associated with the water.

4. A method as defined in claim 3, further comprising:

following the act of determining the conductivity measurement associated with the water, supplying the component chemical product to the solution storage tank to begin formation of the chemical solution therein.

5. A method as defined in claim 4, wherein the act of calculating a conductivity measurement of the chemical solution comprises:
analyzing one or more samples of the chemical solution to generate information related to conductivity of the chemical solution; and
analyzing the information related to the conductivity of the chemical solution to render the conductivity measurement for the chemical solution.

6. A method as defined in claim 1, wherein the analyzing act comprises:
subtracting the conductivity measurement associated with the water from the conductivity measurement of the chemical solution to render an actual conductivity reading for the chemical solution; and
comparing the actual conductivity reading of the chemical solution to the conductivity setpoint.

7. A method as defined in claim 6, further comprising:
if the actual conductivity reading for the chemical solution is less than the conductivity setpoint, requesting that a specified volume of component chemical product be supplied to the solution storage tank.

8. A method as defined in claim 7, wherein the specified volume is defined based on a relative discrepancy between the actual conductivity reading and the conductivity setpoint.

9. A method as defined in claim 7, wherein the specified volume is a predetermined volume that is to be supplied to the solution storage tank each time the actual conductivity reading of the chemical solution is less than the conductivity setpoint.

10. A method as defined in claim 7, further comprising:
if the actual conductivity reading for the chemical solution is greater than the conductivity setpoint, requesting that a specified volume of water be supplied to the solution storage tank.

11. A method as defined in claim 10, wherein the specified volume of water is defined based on a relative discrepancy between the conductivity measurement and the normalized conductivity setpoint.

12. A method as defined in claim 1, wherein the analyzing act comprises:
adding the conductivity measurement associated with the water to the conductivity setpoint to render an normalized conductivity setpoint for the chemical solution; and
comparing the conductivity measurement of the chemical solution to the normalized conductivity setpoint.

13. A method as defined in claim 12, further comprising:
if the conductivity measurement of the chemical solution is less than the normalized conductivity setpoint, requesting that a specified volume of component chemical product be supplied to the solution storage tank.

14. A method as defined in claim 13, wherein the specified volume is defined based on a relative discrepancy between the conductivity measurement and the normalized conductivity setpoint.

15. A method as defined in claim 13, wherein the specified volume is a predetermined volume that is to be supplied to the solution storage tank each time the conductivity measurement of the chemical solution is less than the normalized conductivity setpoint.

16. A method as defined in claim 13, further comprising:
if the conductivity measurement of the chemical solution is greater than the normalized conductivity setpoint, requesting that a specified volume of water be supplied to the solution storage tank.

17. A method as defined in claim 16, wherein the specified volume of water is defined based on a relative discrepancy between the conductivity measurement and the normalized conductivity setpoint.

18. A method as defined in claim 1, wherein the chemical solution in the solution storage tank is used by a warewashing machine for application to articles placed therein during one or more wash processes performed in the warewashing machine.

19. A method as defined in claim 18, wherein the act of determining conductivity measurement associated with the water is performed prior to any of the one or more wash processes being performed in the warewashing machine.

20. A method as defined in claim 19, further comprising:
repeating the calculating and analyzing acts during each of the one or more wash processes performed in the warewashing machine.

21. A method as defined in claim 20, further comprising:
requesting supply of the component chemical product to the solution storage tank if the sum of the conductivity measurement associated with the water and the conductivity setpoint is greater than the conductivity measurement of the chemical solution.

22. A method as defined in claim 21, wherein the requesting act is repeated for each of the one or more wash processes performed in the warewashing machine.

23. A method as defined in claim 20, further comprising:
requesting supply of the component chemical product to the solution storage tank if the conductivity setpoint is greater than a relative difference between the conductivity measurement associated with the water and the conductivity measurement of the chemical solution.

24. A method as defined in claim 23, wherein the requesting act is repeated for each of the one or more wash processes performed in the warewashing machine.

25. A method as defined in claim 1, further comprising:
transmitting at least one of the conductivity measurement for the chemical solution and the conductivity measurement associated with the water to a remote computer over a network connection.

26. A method as defined in claim 1, further comprising:
transmitting results rendered by the analyzing act to a remote computer over a network connection.

27. A system for controlling conductivity of a chemical solution situated in a solution storage tank, the chemical solution being formed by combining at least one component chemical product with water in the solution storage tank, the system comprising:
a sensor sensing first information related to inherent conductivity of the water and second information related to conductivity of the chemical solution, wherein the conductivity of the chemical solution indicates percent concentration of the component chemical product relative to water in the chemical solution; and
a controller communicatively coupled to the sensor for receiving the first and second information and analyzing the first information to render a conductivity reading for the water and the second information to render a conductivity reading for the chemical solution, wherein the controller analyzes the conductivity reading for the water, the conductivity reading for the chemical solution and a conductivity setpoint specified for the chemical solution to determine whether the component chemical product should be supplied to the solution storage tank, wherein the conductivity setpoint indicates a desired percent concentration of the component chemical product relative to water in the chemical solution.

28. A system as defined in claim 27, wherein the sensor comprises an inductive probe.

29. A system as defined in claim 27, wherein the sensor comprises a conductive cell.

30. A system as defined in claim 27, wherein the controller comprises a solid state, non-volatile memory device.

31. A system as defined in claim 27, wherein the chemical solution in the solution storage tank is used by a utility device to perform a task comprising one or more wash processes, wherein the chemical solution is applied to one or more objects during the one or more wash processes.

32. A system as defined in claim 31, wherein the sensor senses the first information and the controller analyzes the first information to render the conductivity reading for the water prior to any of the one or more wash processes being performed.

33. A system as defined in claim 32, wherein the sensor senses the second information, the controller analyzes the second information to render the conductivity reading for the chemical solution, and the controller analyzes the conductivity reading for the water, the conductivity reading for the chemical solution and the conductivity setpoint specified for the chemical solution to determine whether the component chemical product should be supplied to the solution storage tank during each of the one or more wash processes.

34. A system as defined in claim 33, wherein the utility device is a warewashing machine that applies the chemical solution to articles placed therein during the one or more wash processes.

35. A system as defined in claim 27, wherein the controller determines that the component chemical product should be supplied to the solution storage tank if the conductivity setpoint is greater than a relative difference between the conductivity reading for the water and the conductivity reading for the chemical solution.

36. A system as defined in claim 27, wherein the controller determines that the component chemical product should be supplied to the solution storage tank if the sum of the conductivity reading for the water and the conductivity setpoint is greater than the conductivity reading for the chemical solution.

37. A system as defined in claim 27, wherein the controller is connected by a network interface to a communication network, wherein data generated from analyses performed by the controller is transmitted by the network interface to a server computer over the communication network.

38. A system as defined in claim 27, wherein the controller is connected by a network interface to a communication network, wherein the first information and the second information are transmitted by the network interface to a server computer over the communication network.

39. A computer program storage device accessible to a computing system and encoding a computer program for executing a computer process for controlling conductivity of a chemical solution situated in a solution storage tank, the chemical solution being formed by combining at least one component chemical product with water in the solution storage tank, the computer process comprising acts of:
    determining a conductivity measurement associated with the water;
    after the chemical solution is formed in the solution storage tank, calculating a conductivity measurement for the chemical solution, wherein the conductivity measurement indicates a percent concentration of the component chemical product relative to water in the chemical solution; and
    analyzing the conductivity measurement associated with the water, the conductivity measurement of the chemical solution and a conductivity setpoint specified for the chemical solution to determine whether the component chemical product should be supplied to the solution storage tank, wherein the conductivity setpoint indicates a desired percent concentration of the component chemical product relative to water in the chemical solution.

40. A computer program storage device as defined in claim 39, wherein the act of determining a conductivity measurement associated with the water comprises:
    prior to supplying the component chemical product to the solution storage tank, filling the solution storage tank with the water and analyzing one or more samples of the water to generate information related to the conductivity of the water.

41. A computer program storage device as defined in claim 40, wherein the act of determining a conductivity measurement associated with the water further comprises:
    analyzing the information related to the conductivity of the water to render the conductivity measurement associated with the water.

42. A computer program storage device as defined in claim 41, the computer process further comprising:
    following the act of determining the conductivity measurement associated with the water, supplying the component chemical product to the solution storage tank to begin formation of the chemical solution therein.

43. A computer program storage device as defined in claim 42, wherein the act of calculating a conductivity measurement of the chemical solution comprises:
    analyzing one or more samples of the chemical solution to generate information related to conductivity of the chemical solution; and
    analyzing the information related to the conductivity of the chemical solution to render the conductivity measurement for the chemical solution.

44. A computer program storage device as defined in claim 39, wherein the analyzing act comprises:
    subtracting the conductivity measurement associated with the water from the conductivity measurement of the chemical solution to render an actual conductivity reading for the chemical solution; and
    comparing the actual conductivity reading of the chemical solution to the conductivity setpoint.

45. A computer program storage device as defined in claim 44, the computer process comprising:
    if the actual conductivity reading for the chemical solution is less than the conductivity setpoint, requesting that a specified volume of component chemical product be supplied to the solution storage tank.

46. A computer program storage device as defined in claim 45, wherein the specified volume is defined based on a relative discrepancy between the actual conductivity reading and the conductivity setpoint.

47. A computer program storage device as defined in claim 45, wherein the specified volume is a predetermined volume that is to be supplied to the solution storage tank each time the actual conductivity reading of the chemical solution is less than the conductivity setpoint.

48. A computer program storage device as defined in claim 39, wherein the analyzing act comprises:
  adding the conductivity measurement associated with the water to the conductivity setpoint to render an normalized conductivity setpoint for the chemical solution; and
  comparing the conductivity measurement of the chemical solution to the normalized conductivity setpoint.

49. A computer program storage device as defined in claim 48, the computer process further comprising:
  if the conductivity measurement of the chemical solution is less than the normalized conductivity setpoint, requesting that a specified volume of component chemical product be supplied to the solution storage tank.

50. A computer program storage device as defined in claim 49, wherein the specified volume is defined based on a relative discrepancy between the conductivity measurement and the normalized conductivity setpoint.

51. A computer program storage device as defined in claim 49, wherein the specified volume is a predetermined volume that is to be supplied to the solution storage tank each time the conductivity measurement of the chemical solution is less than the normalized conductivity setpoint.

52. A computer program storage device as defined in claim 39, wherein the chemical solution in the solution storage tank is used by a utility device to perform a task comprising one or more wash processes, wherein the chemical solution is applied to one or more objects during the one or more wash processes.

53. A computer program storage device as defined in claim 52, wherein the act of determining conductivity measurement associated with the water is performed prior to any of the one or more wash processes being performed.

54. A computer program storage device as defined in claim 53, the computer process further comprising:
  repeating the calculating and analyzing acts during each of the one or more wash processes.

55. A computer program storage device as defined in claim 54, the computer process further comprising:
  requesting supply of the component chemical product to the solution storage tank if the sum of the conductivity measurement associated with the water and the conductivity setpoint is greater than the conductivity measurement of the chemical solution.

56. A computer program storage device as defined in claim 55, wherein the requesting act is repeated for each of the one or more wash processes.

57. A computer program storage device as defined in claim 54, the computer process further comprising:
  requesting supply of the component chemical product to the solution storage tank if the conductivity setpoint is greater than a relative difference between the conductivity measurement associated with the water and the conductivity measurement of the chemical solution.

58. A computer program storage device as defined in claim 57, wherein the requesting act is repeated for each of the one or more wash processes.

59. A computer program storage device as defined in claim 39, the computer process further comprising:
  transmitting at least one of the conductivity measurement for the chemical solution and the conductivity measurement associated with the water to a remote computer over a network connection.

60. A computer program storage device as defined in claim 39, the computer process further comprising:
  transmitting results rendered by the analyzing act to a remote computer over a network connection.

* * * * *